US012251245B2

(12) United States Patent
Bleas et al.

(10) Patent No.: US 12,251,245 B2
(45) Date of Patent: Mar. 18, 2025

(54) RADIOLOGICAL IMAGING METHOD AND RADIOLOGICAL APPARATUS WITH VERTICAL SCANNING OF 2 RADIATION SOURCES

(71) Applicant: EOS IMAGING, Paris (FR)

(72) Inventors: Stéphane Bleas, Paris (FR); Pascal Desaute, Paris (FR); Laurent Jacquier, Viroflay (FR); Cédric Nottebaert, Villeneuve d'ascq (FR); David Vittecoq, Mere (FR)

(73) Assignee: EOS IMAGING, Paris (FR)

( * ) Notice: Subject to any disclaimer, the term of this patent is extended or adjusted under 35 U.S.C. 154(b) by 265 days.

(21) Appl. No.: 17/774,258

(22) PCT Filed: Nov. 5, 2019

(86) PCT No.: PCT/IB2019/001250
§ 371 (c)(1),
(2) Date: May 4, 2022

(87) PCT Pub. No.: WO2021/090042
PCT Pub. Date: May 14, 2021

(65) Prior Publication Data
US 2022/0386968 A1 Dec. 8, 2022

(51) Int. Cl.
*A61B 6/02* (2006.01)
*A61B 6/00* (2024.01)
(Continued)

(52) U.S. Cl.
CPC ............... *A61B 6/02* (2013.01); *A61B 6/102* (2013.01); *A61B 6/4014* (2013.01); *A61B 6/4007* (2013.01); *A61B 6/4429* (2013.01)

(58) Field of Classification Search
CPC ......... A61B 6/02; A61B 6/102; A61B 6/4007; A61B 6/4014; A61B 6/4429; A61B 6/505;
(Continued)

(56) References Cited

U.S. PATENT DOCUMENTS 7,639,866 B2 * 12/2009 Pomero ............... G06T 7/75
382/128
7,810,996 B1 * 10/2010 Giphart .............. A61B 6/541
378/207

(Continued)

FOREIGN PATENT DOCUMENTS

WO 2019008407 A1 1/2019
WO 2019069001 4/2019

OTHER PUBLICATIONS

International Search Report mailed Jul. 20, 2020, in corresponding to International Application No. PCT/IB2019/001250; 3 pages.
(Continued)

*Primary Examiner* — Dani Fox
*Assistant Examiner* — Soorena Kefayati
(74) *Attorney, Agent, or Firm* — Maier & Maier, PLLC

(57) ABSTRACT

A radiological apparatus including: a gantry encapsulated within a cover, a patient platform, and two radiation sources with imaging directions orthogonal to each other, sliding vertically to perform vertical scanning of a patient standing on the platform. The gantry cover top view is L shaped, each radiation source being located outside the gantry cover, inside the angular sector of the L, and is encapsulated within a cover sliding vertically with the radiation source it encapsulates. The radiological apparatus also includes: a first security device stopping the vertical scanning, when it detects a patient body part going outside a first predetermined area, to avoid collision with the vertically sliding radiation sources covers, and a second security device
(Continued)

stopping the vertical scanning, when it detects an object or a person external to the radiological apparatus within a second predetermined area, to avoid collision with the vertically sliding radiation sources covers.

16 Claims, 6 Drawing Sheets

(51) Int. Cl.
 *A61B 6/10* (2006.01)
 *A61B 6/40* (2024.01)
(58) Field of Classification Search
 CPC . G01V 5/20; G01V 5/22; G01V 5/228; G01V 5/232; G01V 5/222; G01V 5/226; G01V 5/26
 See application file for complete search history.

(56) References Cited

U.S. PATENT DOCUMENTS

| 8,770,838 | B2* | 7/2014 | Papaioannou | A61B 6/4423 |
| | | | | 378/62 |
| 2006/0029181 | A1* | 2/2006 | Chen | A61B 6/4435 |
| | | | | 378/20 |
| 2009/0080598 | A1* | 3/2009 | Tashman | A61B 5/1038 |
| | | | | 378/11 |
| 2012/0130145 | A1* | 5/2012 | Sabol | G16H 30/40 |
| | | | | 600/1 |
| 2012/0307973 | A1* | 12/2012 | Dirauf | A61N 5/1049 |
| | | | | 378/62 |
| 2012/0314836 | A1* | 12/2012 | Smith | G01V 5/222 |
| | | | | 378/57 |
| 2013/0058459 | A1* | 3/2013 | Desaute | G21K 1/04 |
| | | | | 378/62 |
| 2013/0064344 | A1* | 3/2013 | Carol | A61B 6/04 |
| | | | | 378/10 |
| 2016/0051211 | A1* | 2/2016 | Linev | A61B 6/4405 |
| | | | | 378/62 |
| 2020/0320687 | A1* | 10/2020 | Colobert | A61B 6/5247 |

OTHER PUBLICATIONS

Written Opinion of the International Searching Authority mailed Jul. 20, 2020, in corresponding to International Application No. PCT/IB2019/001250; 6 pages.

* cited by examiner

RADIOLOGICAL IMAGING METHOD AND RADIOLOGICAL APPARATUS WITH VERTICAL SCANNING OF 2 RADIATION SOURCES

FIELD

The invention relates to radiological imaging methods and radiological apparatus with vertical scanning of 2 radiation sources.

BACKGROUND

In a prior art, it is known a radiological apparatus comprising a gantry encapsulated within a cover, a patient platform, 2 radiation sources with imaging directions orthogonal to each other, sliding vertically so as to perform vertical scanning of a patient standing on said platform, in which these 2 radiation sources are also encapsulated with the gantry in a single and same cover which is the one and single cover of the whole radiological apparatus.

However, this radiological apparatus presents the drawbacks of being rather bulky and of having at the same time little accessibility to platform for standard patients, let alone for corpulent or obese patients.

In order to warrant security of radiological apparatus and especially safety of patient, all moving parts including the 2 radiation sources vertically sliding to perform vertical scanning of the patient when imaging the patient standing on the patient platform, are encapsulated within a single and big cover so that no moving part and especially no vertically sliding radiation source can collide with patient or with other object like a chair or a box for example. There is a one and single big global cover for the whole radiological apparatus.

SUMMARY

The object of the present invention is to alleviate at least partly the above mentioned drawbacks.

More particularly, the invention aims to improve compromise between apparatus compactness and patient accessibility, while simultaneously keeping a sufficiently good level of security.

Indeed, the technical problem contemplated by the invention is how to improve the compromise between radiological apparatus global compactness on the one side and patient accessibility, especially corpulent or even obese patient accessibility, on the other side, while at the same time, still keeping a good level of security, at least a reasonable level of security, especially with respect to patient safety during imaging performing.

The invention proposes a solution where the global shape of the gantry cover is completely different from the one of the prior art, with 2 radiation sources being outside gantry cover and having respectively their own covers vertically sliding, while at the same time including security devices which protect patient from collision with sliding radiations sources as well as protect sliding radiation sources from collision with objects external to the radiological apparatus.

This object is achieved with a radiological imaging method comprising: vertical scanning, of a patient standing on a patient platform, by 2 radiation sources which belong to a gantry encapsulated within a cover, which have imaging directions orthogonal to each other and which slide vertically so as to perform said vertical scanning, wherein: said gantry cover top view is L shaped, each of said 2 radiation sources: is located outside said L shaped gantry cover, inside angular sector of said L, and is encapsulated within a cover sliding vertically with said radiation source it encapsulates, and wherein it also comprises: a first security device stopping said vertical scanning, when it detects a patient body part going outside a first predetermined area, so as to avoid collision between said patient body part and said vertically sliding radiation sources covers, and a second security device stopping said vertical scanning, when it detects presence of an object or of a person external to said radiological apparatus within a second predetermined area, so as to avoid collision between said object or person and said vertically sliding radiation sources covers.

Preferably, said 2 security devices emit electromagnetic radiation beams and: said first security device stops said vertical scanning, when one or more of its emitted radiation beam(s) is crossed by a patient body part going outside said first predetermined area, so as to avoid collision between said patient body part and said vertically sliding radiation sources covers, and said second security device stops said vertical scanning, when one or more of its emitted radiation beam(s) is crossed by presence of an object or of a person external to said radiological apparatus within a second predetermined area, so as to avoid collision between said object or person and said vertically sliding radiation sources covers. Hence, crossing emitted radiation beam is a simple and efficient way to detect presence of unwanted body or object, allowing for keeping a high security standard, while simultaneously not making security system too complex, despite radiation sources vertically sliding outside gantry cover.

Preferably, said first predetermined area is different from said second predetermined area. Advantageously, said first predetermined area is fully disjoint from said second predetermined area, meaning intersection of said first predetermined area and of said second predetermined area is void.

This object is also achieved with a radiological apparatus comprising: a gantry encapsulated within a cover, a patient platform, 2 radiation sources with imaging directions orthogonal to each other, sliding vertically so as to perform vertical scanning of a patient standing on said platform, wherein: said gantry cover top view is L shaped, each of said 2 radiation sources: is located outside said L shaped gantry cover, inside angular sector of said L, and is encapsulated within a cover sliding vertically with said radiation source it encapsulates, and wherein said radiological apparatus also comprises: a first security device stopping said vertical scanning, when it detects a patient body part going outside a first predetermined area, so as to avoid collision between said patient body part and said vertically sliding radiation sources covers, and a second security device stopping said vertical scanning, when it detects presence of an object or of a person external to said radiological apparatus within a second predetermined area, so as to avoid collision between said object or person and said vertically sliding radiation sources covers.

More generally speaking, the object of improving compromise between apparatus compactness and patient accessibility, while not caring about the level of security could be fulfilled by a radiological apparatus comprising: a gantry encapsulated within a cover, a patient platform, 2 radiation sources with imaging directions orthogonal to each other, sliding vertically so as to perform vertical scanning of a patient standing on said platform, wherein: said gantry cover top view is L shaped, each of said 2 radiation sources: is located outside said L shaped gantry cover, inside angular sector of said L, and is encapsulated within a cover sliding vertically with said radiation source it encapsulates.

Preferred embodiments comprise one or more of the following features, which can be taken separately or together, either in partial combination or in full combination, with one or the other of preceding objects of the invention.

Preferably, in a square array having three rows from A to C and three columns from 1 to 3: said L shaped gantry cover top view recovers squares C1, C2, C3, B3, A3, said 2 radiation sources covers are respectively located within squares B1 and A2, said patient platform recovers square B2, square A1 remains entirely free and void.

Hence, the compromise between radiological apparatus global compactness on the one side and patient accessibility, especially corpulent or even obese patient accessibility, on the other side, is still improved, without giving up security and safety level.

Preferably, said 2 security devices emit electromagnetic radiation beams and: said first security device stops said vertical scanning, when one or more of its emitted radiation beam(s) is crossed by a patient body part going outside said first predetermined area, so as to avoid collision between said patient body part and said vertically sliding radiation sources covers, and said second security device stops said vertical scanning, when one or more of its emitted radiation beam(s) is crossed by presence of an object or of a person external to said radiological apparatus within a second predetermined area, so as to avoid collision between said object or person and said vertically sliding radiation sources covers.

Hence, crossing emitted radiation beam is a simple and efficient way to detect presence of unwanted body or object, allowing for keeping a high security standard, while simultaneously not making security system too complex, despite radiation sources vertically sliding outside gantry cover.

Preferably, said first predetermined area encompasses a space located above said platform or encompasses only a space located above said platform.

Hence, for a given compromise between radiological apparatus global compactness on the one side and patient accessibility, especially corpulent or even obese patient accessibility, on the other side, the security and safety level is still improved.

Preferably, said first security device includes 2 vertical fan beam sensors, preferably radars or lidars, preferably respectively located in the middle of internal faces of branches of said L.

Hence, for a given compromise between radiological apparatus global compactness on the one side and patient accessibility, especially corpulent or even obese patient accessibility, on the other side, the security and safety level is still improved.

Preferably, said second predetermined area encompasses a vicinity of paths of said vertically sliding radiation sources covers or encompasses a space located both below lower ends of paths of said vertically sliding radiation sources covers and above ground on which stands said radiological apparatus.

Hence, for a given compromise between radiological apparatus global compactness on the one side and patient accessibility, especially corpulent or even obese patient accessibility, on the other side, the security and safety level is still improved.

Preferably, said second security device includes 2 horizontal fan beam sensors, preferably radars or lidars, preferably respectively located at lower ends of internal faces of branches of said L.

Hence, for a given compromise between radiological apparatus global compactness on the one side and patient accessibility, especially corpulent or even obese patient accessibility, on the other side, the security and safety level is still improved.

Preferably, said platform is supported by an elevator lifting vertically a patient standing on said platform.

Hence, patient accessibility, especially corpulent or even obese patient accessibility, is still improved, without giving up achievement performed on radiological apparatus global compactness. Indeed, platform is at low level to help patient stepping on it, and then only afterwards, is platform brought to a higher level adequate for performing patient radiological imaging.

Preferably, a ratio between on the one side a width of a branch of said L shaped gantry cover top view and on the other side a length of said branch of said L shaped gantry cover top view is in the range 30-40%.

Hence, achievement performed on radiological apparatus global compactness is still improved.

Preferably, each radiation source cover has a beveled part pointing towards said platform.

Hence, security and especially patient safety are still improved, since on the one side, even in case of deficiency of security devices, collision between vertically sliding radiation source and moving patient would be softer, and since on the other side, the bulk of radiation source close to patient face is smaller thereby being less oppressive to patient and therefore lowering the risk of untimely patient move which, even when managed by security devices stopping vertical scanning of radiation sources, are still detrimental because they need starting all over again this vertical scanning of the patient.

Preferably, top end position along the path of vertically sliding radiation source cover is more than 1.90 m or more than 2.00 m above lowest part of said radiological apparatus.

Preferably, bottom end position along the path of vertically sliding radiation source cover is comprised between 20 mm and 70 mm or between 30 mm and 60 mm above lowest part of said radiological apparatus.

Hence, patient accessibility, especially corpulent or even obese patient accessibility, as well as tall patient or giant patient accessibility, is still improved, without negatively impacting the global surface on the ground occupied by the radiological apparatus, thereby improving patient accessibility at no practical cost relative to radiological apparatus compactness.

Preferably, on internal face of each branch of said L, there is a gutter recovered by a vertical strip which has a sliding opening and which is interdependent with corresponding vertically sliding radiation source cover.

Hence, security and patient safety (in case patient would for instance try and put a hand or a finger within one of these gutters) are improved without degrading the achievement performed on radiological apparatus global compactness.

Advantageously, said first predetermined area is different from said second predetermined area. Advantageously, said first predetermined area is fully disjoint from said second predetermined area, meaning intersection of said first predetermined area and of said second predetermined area is void.

These radiation sources are advantageously X-ray sources and/or 2D (two dimensional) radiation sources, and more advantageously 2D X-ray sources, 2D sources are planar sources. One of these radiation sources advantageously gives a front view of standing patient body or of part of standing patient body, whereas the other of these radiation sources advantageously gives a lateral view or a side view of standing patient body or of part of standing patient body.

As an alternative to what just precedes, instead of an X-ray source with vertical scanning, an optical camera with vertical scanning may be used, or an hybrid system with both an X-ray source with vertical scanning and an optical camera with vertical scanning. This could be used both for frontal imaging and for lateral imaging.

Advantageously, the patient platform is located at intersection of two branches of said L, meaning in the corner at intersection of internal faces of branches of said L.

Advantageously, within the rear face of gantry cover, at the opposite of the angular sector of L shape, there is a door giving direct access to electrical cabinet of pantry.

As an alternative or as a complementary aspect to all what precedes, focusing mostly on the object of improving compromise between apparatus compactness and patient accessibility, while favoring especially patient accessibility, can be achieved by a radiological apparatus comprising:
- a gantry encapsulated within a cover, a patient platform, 2 radiation sources with imaging directions orthogonal to each other, sliding vertically so as to perform vertical scanning of a patient standing on said platform, wherein: said gantry cover top view is L shaped, each of said 2 radiation sources: is located outside said L shaped gantry cover, inside angular sector of said L, and is encapsulated within a cover sliding vertically with said radiation source it encapsulates,
- and/or a patient platform which height is adjustable by an elevator located under said patient platform, preferably located at intersection of two branches of said L,
- and/or a patient holding horizontal bar which height is adjustable by sliding along a vertical rail,
- and/or a patient holding vertical bar which is fixed.

Such compromise is most preferably achieved by:
- a radiological apparatus comprising: a gantry encapsulated within a cover, a patient platform, 2 radiation sources with imaging directions orthogonal to each other, sliding vertically so as to perform vertical scanning of a patient standing on said platform, wherein: said gantry cover top view is L shaped, each of said 2 radiation sources: is located outside said L shaped gantry cover, inside angular sector of said L, and is encapsulated within a cover sliding vertically with said radiation source it encapsulates, and a patient platform which height is adjustable by an elevator located under said patient platform, preferably located at intersection of two branches of said L, and a patient holding horizontal bar which height is adjustable by sliding along a vertical rail.

Alternatively, is also contemplated:
- a radiological apparatus comprising: a gantry encapsulated within a cover, a patient platform, wherein: said gantry cover top view is L shaped, and a patient platform which height is adjustable by an elevator located under said patient platform, located at intersection of two branches of said L, and a patient holding horizontal bar which height is adjustable by sliding along a vertical rail.

Further features and advantages of the invention will appear from the following description of embodiments of the invention, given as non-limiting examples, with reference to the accompanying drawings listed hereunder.

DETAILED DESCRIPTION

Figure 1:
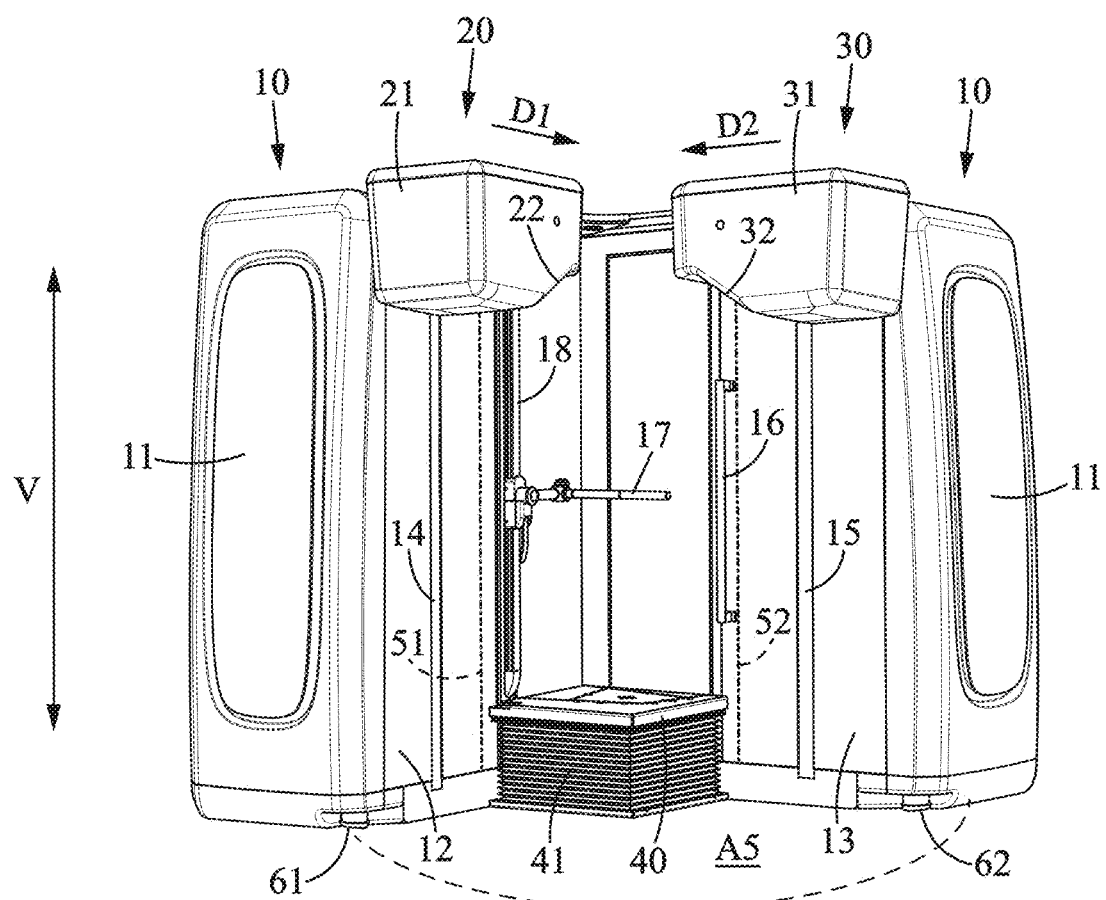
FIG. 1 shows a perspective front view of an example of a radiological apparatus according to an embodiment of the invention.

FIG. 1 shows a perspective front view of an example of a radiological apparatus according to an embodiment of the invention.

The radiological apparatus comprises a gantry 10 encapsulated within a cover 11, a patient platform 40, 2 radiation sources 20 and 30 with imaging directions D1 and D2 orthogonal to each other, sliding vertically (along direction V) so as to perform vertical scanning of a patient standing on platform 40. The patient standing on platform 40 is scanned vertically, either from top to down, or from bottom to up, by the 2 radiations sources 20 and 30.

Figure 4:
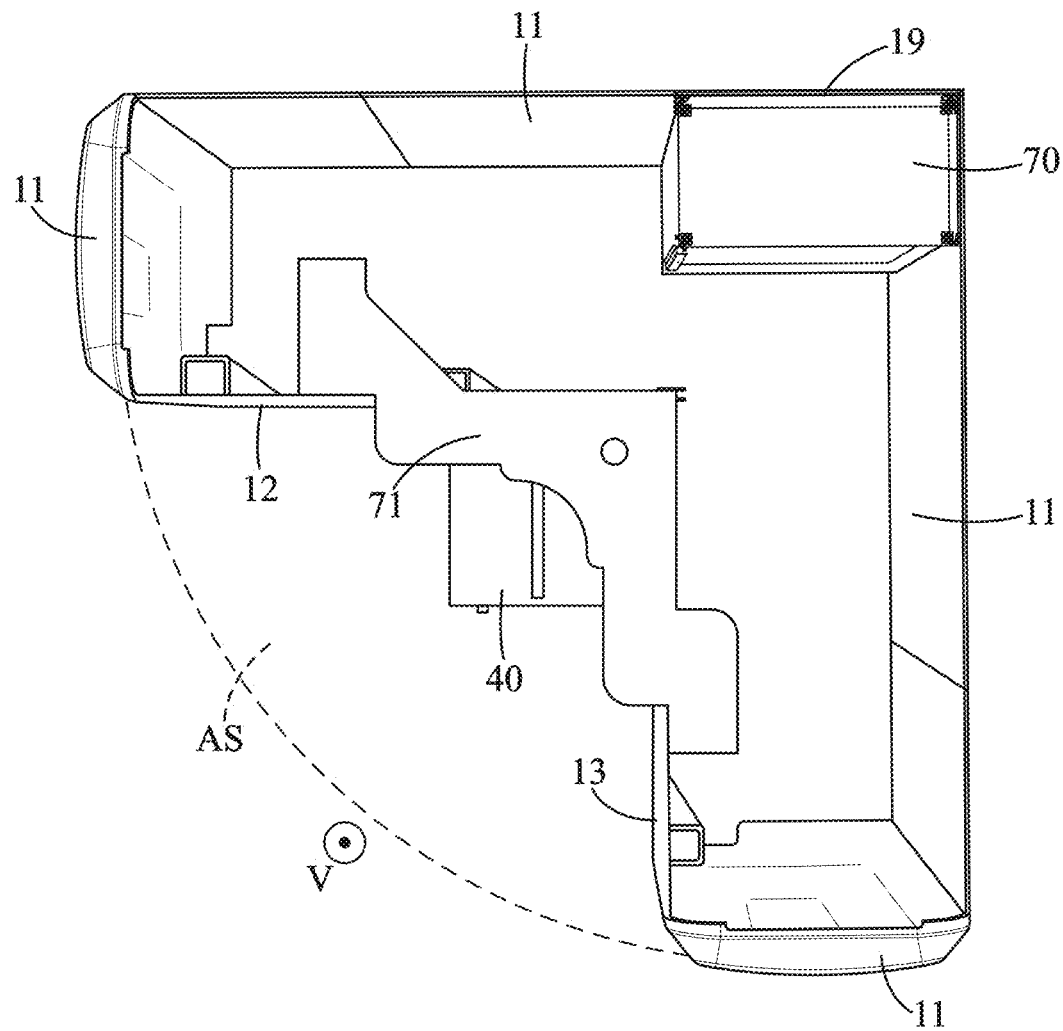
FIG. 4 shows a top view of an example of a radiological apparatus according to an embodiment of the invention, with the top cover of gantry withdrawn.
Figure 5:
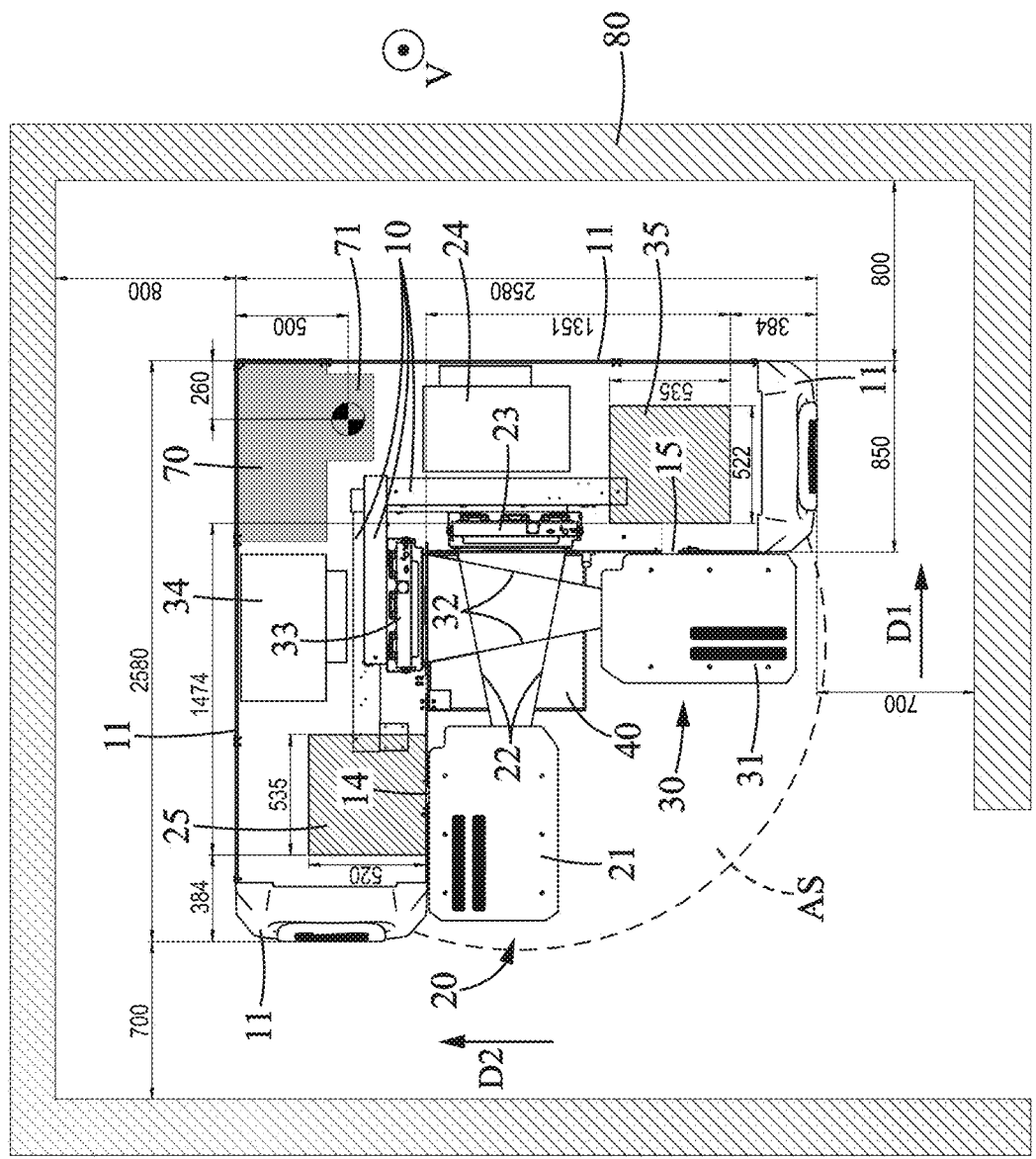
FIG. 5 shows a top view of an example of a radiological apparatus according to an embodiment of the invention, with the top cover of gantry withdrawn, and with inside of the gantry cover partly visible.
Figure 6:
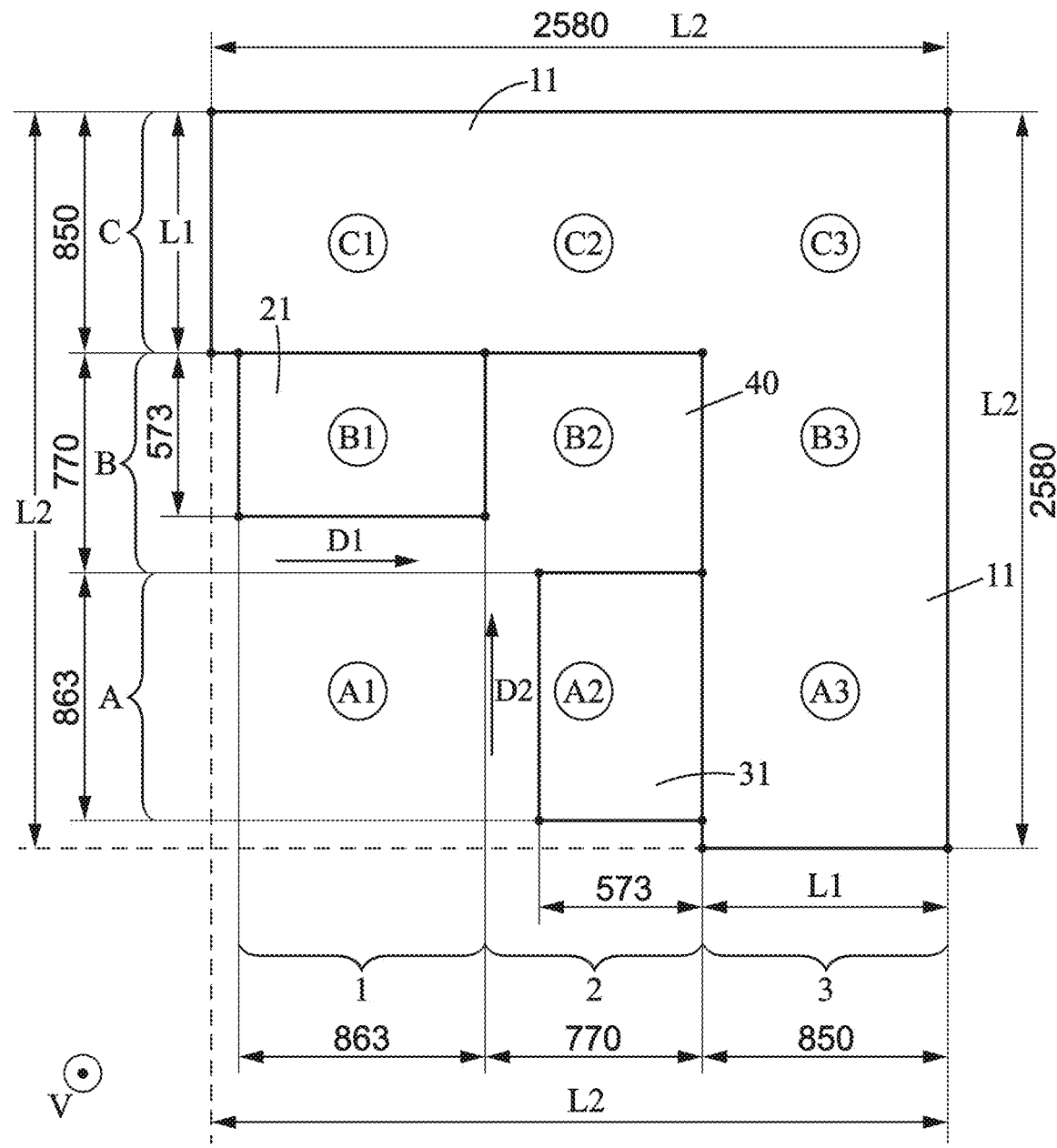
FIG. 6 shows schematically a top view of an example of a radiological apparatus according to an embodiment of the invention, showing occupation of the ground within an array having A/B/C lines and 1/2/3 columns.

The gantry cover 11 top view is L shaped, as best visible on FIGS. 4 to 6.

Radiation source 20 is located outside said L shaped gantry cover 11, inside angular sector AS of said L, which means radiation source 20 is located between internal faces 12 and 13 of the L shape of gantry cover 11, and radiation source 20 is encapsulated within a cover 21 sliding vertically with said radiation source 20 it encapsulates. On internal face 12 of one of the branches of the L shape of gantry cover 11, there is a gutter recovered by a vertical strip which has a sliding opening and which is interdependent with corresponding vertically sliding radiation source cover 21, which means that depending on radiation source cover 21 going up or down, this strip 14 opens to let the radiation source cover 21 slide and closes just after the radiation source cover 21 has gone by. The angular sector AS is the region located between the 2 plans corresponding to internal faces 12 and 13, this region comprises the platform 40, this region excludes the gantry cover 11 and all space behind this gantry cover 11, this region corresponds to a quarter of the space starting at the right angle where internal faces 12 and 13 intersect.

Radiation source 30 is located outside said L shaped gantry cover 11, inside angular sector AS of said L, which means radiation source 30 is located between internal faces 12 and 13 of the L shape of gantry cover 11, and radiation source 30 is encapsulated within a cover 31 sliding vertically with said radiation source 30 it encapsulates. On internal face 13 of the other branch of the L shape of gantry cover 11, there is a gutter recovered by a vertical strip 15 which has a sliding opening and which is interdependent with corresponding vertically sliding radiation source cover 31, which means that depending on radiation source cover 31 going up or down, this strip 15 opens to let the radiation source cover 31 slide and closes just after the radiation source cover 31 has gone by.

The radiological apparatus also comprises 2 security devices which both emit electromagnetic radiation beams.

There is a first security device which stops the vertical scanning, when at least either emitted radiation beam 51 or emitted radiation beam 52 is crossed by a patient body part going outside a first predetermined area, so as to avoid collision between patient body part and vertically sliding radiation sources covers 21 and 31. The first predetermined area encompasses a space located above the platform 40 or encompasses only a space located above the platform 40. The first security device includes 2 vertical fan beam sensors 51 and 52, either radars or lidars, respectively located in the middle of internal faces 12 and 13 of branches of L shape of the gantry cover 11.

There is also a second security device which stops the vertical scanning, when at least either emitted radiation beam 61 or emitted radiation beam 62 is crossed by presence of an object or of a person external to radiological apparatus within a second predetermined area, so as to avoid collision between this object or person and said vertically sliding radiation sources covers 21 and 31. The second predetermined area encompasses a vicinity of paths of the vertically sliding radiation sources covers 21 and 31 or encompasses a space located both below lower ends of paths of the vertically sliding radiation sources covers 21 and 31 and above ground on which stands the radiological apparatus. The second security device includes 2 horizontal fan beam sensors 61 and 62, either radars or lidars, respectively located at lower ends of internal faces 12 and 13 of branches of said L shape of the gantry cover 11.

The platform 40 is supported by an elevator 41 lifting vertically a patient standing on this platform 41. On FIG. 1, platform 40 is in high position, and elevator 41 is extended.

Radiation source cover 21 has a beveled part 22 pointing towards platform 40. Radiation source cover 31 has a beveled part 32 pointing towards platform 40.

The top end position along the path of vertically sliding radiation source cover 21 or 31 is more than 1.90 m or more than 2.00 m above lowest part of the radiological apparatus, which means that a patient of a height respectively less than 1.90 m or 2.00 m can walk under these radiation source covers 21 or 31 without bumping or hurting his or her head into them.

The bottom end position along the path of vertically sliding radiation source cover 21 or 31 is comprised between 20 mm and 70 mm or between 30 mm and 60 mm above lowest part of the radiological apparatus, and hence comprised between 20 mm and 70 mm or between 30 mm and 60 mm above the ground on which lies the radiological apparatus.

There is, on the internal face 13 of gantry cover 11, a vertical holding bar 16 to help patient standing, and also to help patient climbing on the platform 40, which may still be a 10 cm step to climb even when the elevator 41 is fully retracted, as well as to help patient standing on platform 40 to secure his or her position when elevator 41 is extending to upper position of platform 40. This vertical holding bar 16 is fixed, and is located just above one corner of platform 40. This corner is a corner next to internal face 13 but not the corner intersecting with internal face 12. There is also, on the internal face 12 of gantry cover 11, a vertical rail 18 along which a horizontal holding bar 17, also to help patient standing, can slide and be fixed at any wished height within a predetermined range, so as to fit different possible heights of patients standing on platform 40 which itself can be fixed at any wished height within a predetermined range, thanks to elevator 41. This vertical rail 18 is fixed, and is located just above one corner of platform 40. This corner is a corner next to internal face 12 but not the corner intersecting with internal face 13.

Figure 2:
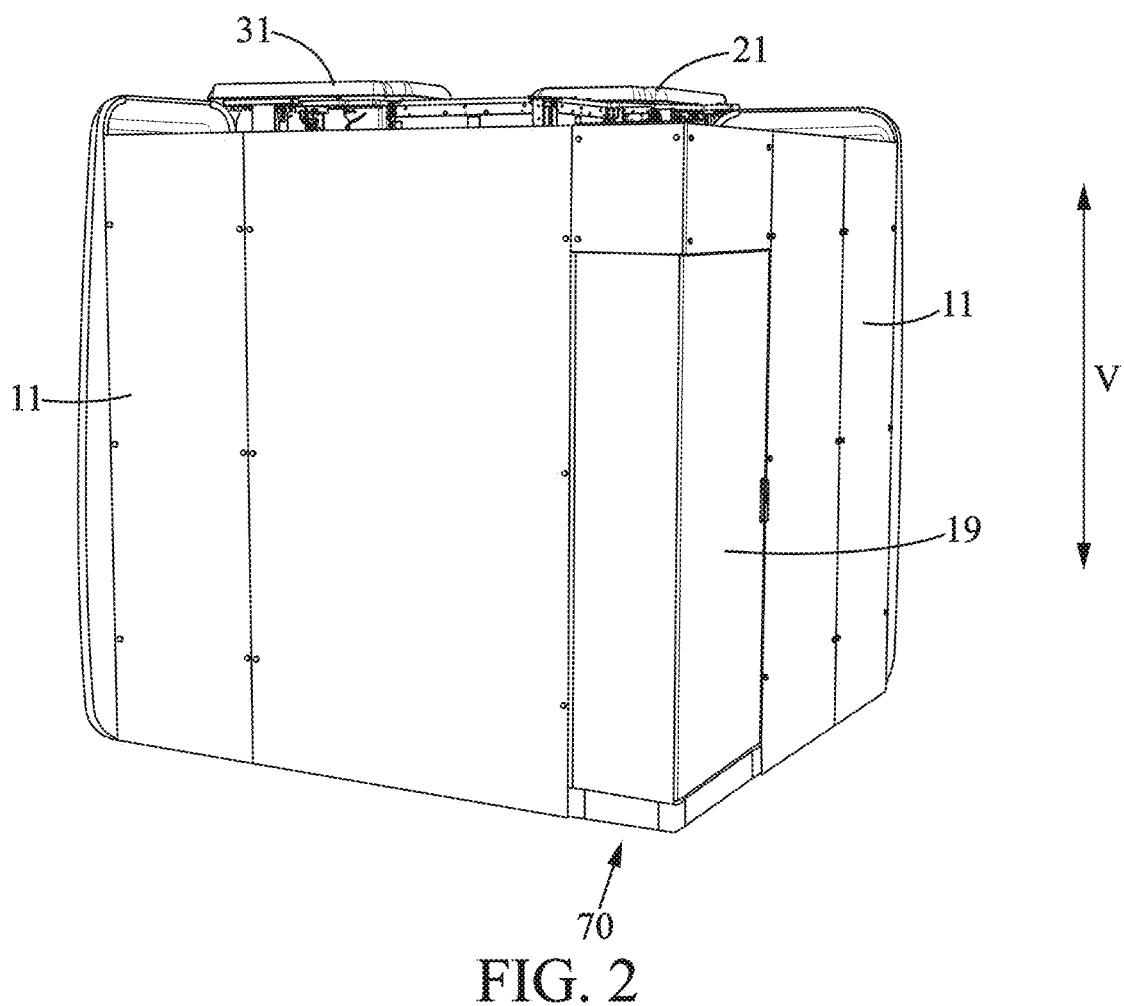
FIG. 2 shows a perspective rear view of an example of a radiological apparatus according to an embodiment of the invention.

FIG. 2 shows a perspective rear view of an example of a radiological apparatus according to an embodiment of the invention.

On the rear side of gantry cover 11, there is a rear door 19 which, when opened, will give direct access to an electrical cabinet 70 where all electrical connections of the gantry 10 are gathered together.

Figure 3:
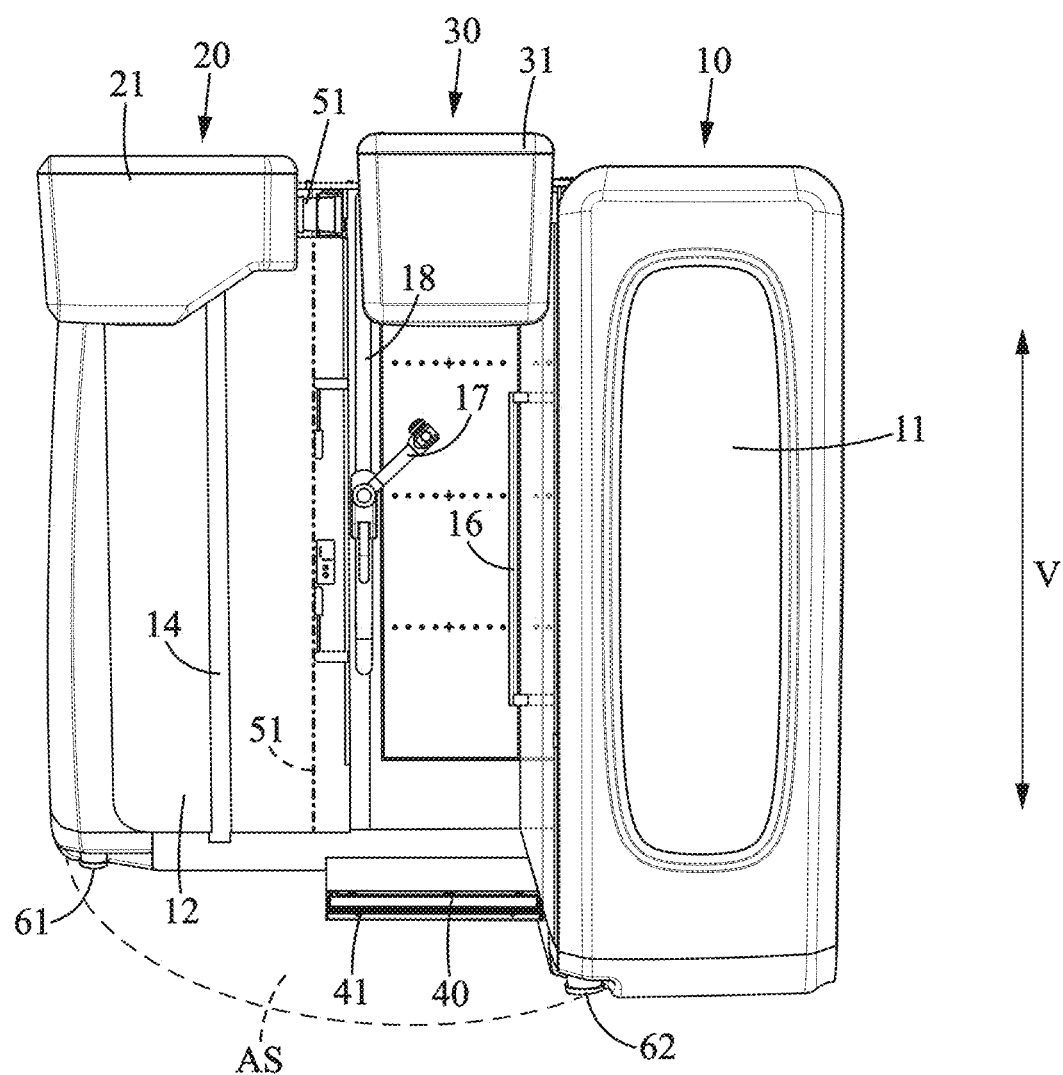
FIG. 3 shows a lateral or side view of an example of a radiological apparatus according to an embodiment of the invention.

FIG. 3 shows a lateral or side view of an example of a radiological apparatus according to an embodiment of the invention.

On FIG. 3, platform 40 is in low position, and elevator 41 is retracted.

One can see that a patient can easily step on the platform 40 before elevator 41 is extended and platform 40 is raised to a wished level. All space above platform 40 is available for standing patient which can grip either vertical holding bar 16 and/or horizontal holding bar 17 which height is adjustable by the sliding of this horizontal holding bar 17 along vertical rail 18, as well as height of platform 40 is adjustable by extension or retraction of elevator 41.

FIG. 4 shows a top view of an example of a radiological apparatus according to an embodiment of the invention, with the top cover of gantry withdrawn.

At the top of gantry cover 11 there is a central reinforcement plate 71 which strengthens together the internal faces 12 and 13. This central reinforcement plate 71 has globally an L shape and is located within the angular sector AS made by the 2 branches of the L shape gantry cover 11, at the level of the intersection of these internal faces 12 and 13.

FIG. 5 shows a top view of an example of a radiological apparatus according to an embodiment of the invention, with the top cover of gantry withdrawn, and with inside of the gantry cover partly visible.

Close to electrical cabinet 70, there is the electrical cabling interface 71, where electrical power from outside can be brought in.

Along first imaging direction D1, one can see in successive line: the first radiation source 20 encapsulated within first radiation source cover 21, the emitted X-ray beam 22 arriving on the first detector 23 which is already within gantry cover 11, an arm of gantry 10. The first radiation source cover 21 slides vertically along a first column 25 linked and fixed to the arm of gantry 10. The unit 34 is the generator for the radiation source 20. The translation stage of column 25 also holds the radiation source 20, the radiation source cover 21, and the strip 14. The first detector 23 is directly supported by the arm of gantry 10.

Along second imaging direction D2, one can see in successive line: the second radiation source 30 encapsulated within second radiation source cover 31, the emitted X-ray beam 32 arriving on the second detector 33 which is already within gantry cover 11, another arm of gantry 10. The second radiation source cover 31 slides vertically along a second column 35 linked and fixed to the other arm of gantry 10. The second detector 33 is directly supported by the other arm of gantry 10.

Both arms of gantry 10 can be fixed together, or more preferably they can be separate and independent from each other, making two separate and independent arms of gantry 10, each advantageously being of a C shape. The unit 24 is the generator for the radiation source 30. The translation stage of column 35 also holds the radiation source 30, the radiation source cover 31, and the strip 15.

The central reinforcement plate 71 (visible on FIG. 4) is fixed on the top of the two columns 25 and 35, in order to strengthen together these two vertical columns 25 and 35.

X-ray emitted beams 22 and 32, which are orthogonal to each other, cross each other within a region located above platform 40 where the patient will be standing. Therefore, first X-ray emitted beam 22 will make a frontal image of standing patient on sensitive surface of first detector 23, whereas second X-ray emitted beam 32 will make a side image of standing patient on sensitive surface of second detector 33. Frontal image and lateral (or side) image are taken along directions D1 and D2 which are orthogonal to each other.

FIG. 6 shows schematically a top view of an example of a radiological apparatus according to an embodiment of the invention, showing occupation of the ground within an array having A/B/C lines and 1/2/3 columns.

In a square array having three rows from A to C and three columns from 1 to 3, the L shaped gantry cover 11 top view recovers squares C1, C2, C3, B3, A3, the 2 radiation sources covers 21 and 31 are respectively located within squares B1 and A2, and the platform 40 recovers square B2, whereas square A1 remains entirely free and void.

The ratio between on the one side a width L1 of a branch of said L shaped gantry cover 11 top view and on the other side a length L2 of said branch of said L shaped gantry cover top view is in the range 30-40%. On FIG. 6, this ratio value is about 33% (8.50 mm/2580 mm).

All values of dimensions are given in mm (millimeters): for example the length (L2) of a branch of the L shaped gantry cover 11 is 2580 mm, and for example the length of a radiation source cover 21 or 31 is 863 mm, and for example the width of a radiation source cover 21 or 31 is 573 mm, and for example the width (L1) of a branch of the L shaped gantry cover 11 is 850 mm.

The invention has been described with reference to preferred embodiments. However, many variations are possible within the scope of the invention.

The invention claimed is:

1. A radiological imaging method comprising:
    vertical scanning, of a patient standing on a patient platform, by a first radiation source and a second radiation source which belong to a gantry encapsulated within a gantry cover, which have imaging directions orthogonal to each other and which slide vertically so as to perform said vertical scanning, wherein:
    said gantry cover has a top view that is L shaped and has an interior angular sector,
    each of said first and second radiation sources:
        is located:
            outside of said L shaped gantry cover, and
            inside of the interior angular sector,
        and is encapsulated within a cover sliding vertically with said radiation source that said cover encapsulates;
    detecting, using a first security device, a patient body part going outside a first predetermined area;
    stopping, using said first security device, said vertical scanning when said first security device detects a patient body part going outside a first predetermined area so as to avoid collision between said patient body part and said vertically sliding radiation sources covers;
    detecting, using a second security device, a presence of an object or of a person external to said radiological apparatus within a second predetermined area; and
    stopping, using said second security device, said vertical scanning when said second security device detects the presence of an object or of a person external to said radiological apparatus within the second predetermined area so as to avoid collision between said object or person and said vertically sliding radiation sources covers.

2. The radiological imaging method according to claim 1, wherein:
    the first and second security devices emit electromagnetic radiation beams, and
    wherein the method further comprises:
    stopping, using said first security device, said vertical scanning when the emitted radiation beams cross the patient body part going outside said first predetermined area so as to avoid collision between said patient body part and said vertically sliding radiation sources covers; and
    stopping, using said second security device, said vertical scanning when the emitted radiation beams cross by the presence of the object or of the person external to said radiological apparatus within a second predetermined area so as to avoid collision between said object or person and said vertically sliding radiation sources covers.

3. A radiological apparatus comprising:
    a gantry encapsulated within a gantry cover,
    a patient platform,
    a first radiation source and a second radiation source with imaging directions orthogonal to each other, sliding vertically so as to perform vertical scanning of a patient standing on said platform,
    wherein:
    said gantry cover has a top view is L shaped and has an interior angular sector,
    each of said first and second radiation sources:
        is located:
            outside of said L shaped gantry cover, and
            inside of the interior angular sector,
        and is encapsulated within a cover sliding vertically with said radiation source that the cover encapsulates,
    a first security device stopping said vertical scanning, when said first security device detects a patient body part going outside a first predetermined area, so as to avoid collision between said patient body part and said vertically sliding radiation sources covers,
    and a second security device stopping said vertical scanning, when said second security device detects presence of an object or of a person external to said radiological apparatus within a second predetermined area, so as to avoid collision between said object or person and said vertically sliding radiation sources covers.

4. The radiological apparatus according to claim 3, wherein:
    in a square array having six equal sized squares labeled A1-A3, B1-B3, and C1-C3:
    said L shaped gantry cover top view recovers squares C1, C2, C3, B3, A3,
    said 2 radiation sources covers are respectively located within squares B1 and A2,
    said patient platform covers square B2,
    square A1 remains entirely free and void.

5. The radiological apparatus according to claim 3, wherein:
    the first and second security devices emit electromagnetic radiation beams and:

said first security device stops said vertical scanning, when one or more of its emitted radiation beam(s) is crossed by a patient body part going outside said first predetermined area, so as to avoid collision between said patient body part and said vertically sliding radiation sources covers, and said second security device stops said vertical scanning, when the emitted radiation beams cross the presence of the object or of the person external to said radiological apparatus within a second predetermined area, so as to avoid collision between said object or person and said vertically sliding radiation sources covers.

6. The radiological apparatus according to claim 3, wherein said first predetermined area encompasses a space located above said platform or encompasses only a space located above said platform.

7. The radiological apparatus according to claim 3, wherein said second predetermined area encompasses a vicinity of paths of said vertically sliding radiation sources covers or encompasses a space located both below lower ends of paths of said vertically sliding radiation sources covers and above ground on which stands said radiological apparatus.

8. The radiological apparatus according to claim 3, wherein said platform is supported by an elevator lifting vertically a patient standing on said platform.

9. The radiological apparatus according to claim 3, wherein said L shaped gantry cover top view has two branches, and wherein a ratio between a width of a branch of the two branches of said L shaped gantry cover top view and a length of said branch of the two branches of said L shaped gantry cover top view is in the range 30-40%.

10. The radiological apparatus according to claim 3, wherein each radiation source cover has a beveled part pointing towards said platform.

11. The radiological apparatus according to claim 3, wherein a top end position along the path of vertically sliding radiation source cover is more than 1.90 m or more than 2.00 m above a bottom of said radiological apparatus.

12. The radiological apparatus according to claim 3, wherein a bottom end position along the path of vertically sliding radiation source cover is between 20 mm and 70 mm or between 30 mm and 60 mm above a bottom of said radiological apparatus.

13. The radiological apparatus according to claim 3, further comprising: a gutter located on an internal face of each branch of the L shaped gantry and is covered by a vertical strip that has a sliding opening, wherein the vertical strip is interdependent with the corresponding vertically sliding radiation source cover.

14. The radiological apparatus according to claim 6, wherein said first security device includes either two vertical fan beam sensors or two vertical fan beam sensors that are radars or lidars, which are or are not respectively located in the middle of internal faces of branches of said L.

15. The radiological apparatus according to claim 7, wherein said second security device includes either two horizontal fan beam sensors or two horizontal fan beam sensors that are radars or lidars, which are or are not respectively located at lower ends of internal faces of branches of said L.

16. A radiological apparatus comprising:
a gantry encapsulated within a gantry cover,
a patient platform,
a first radiation source and a second radiation source with imaging directions orthogonal to each other, sliding vertically so as to perform vertical scanning of a patient standing on said platform,
wherein:
said gantry cover has a top view that is L shaped and has an interior angular sector,
each of said first and second radiation sources:
is located:
outside of said L shaped gantry cover,
inside of the interior angular sector,
and is encapsulated within a cover sliding vertically with said radiation source that said cover encapsulates.

* * * * *